United States Patent [19]

Karler

[11] 4,073,897
[45] Feb. 14, 1978

[54] TREATMENT OF ARTHRITIS AND ALLIED CONDITIONS WITH XENYLSALATE

[75] Inventor: Arthur Karler, Berkeley, Calif.

[73] Assignee: Diagnostic Data, Inc., Mountain View, Calif.

[21] Appl. No.: 741,547

[22] Filed: Nov. 15, 1976

[51] Int. Cl.$^2$ ............................................. A61K 31/60
[52] U.S. Cl. ..................................................... 424/230
[58] Field of Search ................................ 424/230, 308

[56] References Cited

U.S. PATENT DOCUMENTS

| | | | |
|---|---|---|---|
| 2,594,350 | 4/1952 | Sahyum | 260/473 S |
| 3,466,372 | 9/1969 | Shen et al. | 424/308 |
| 3,657,430 | 4/1972 | Shen et al. | 424/308 |
| 3,859,338 | 1/1975 | Engel | 424/308 |

Primary Examiner—Stanley J. Friedman
Attorney, Agent, or Firm—Robert G. Slick

[57] ABSTRACT

Xenylsalate hydrochloride taken systemically, either orally or subcutaneously, has been found to be an effective relief for the symptoms of arthritis and allied conditions. Substantially no side effects have been noted.

4 Claims, No Drawings

TREATMENT OF ARTHRITIS AND ALLIED CONDITIONS WITH XENYLSALATE

SUMMARY OF THE INVENTION

At the present time, the most popular treatment for the relief of arthritis is aspirin. Aspirin is not fully effective for this purpose and has undesirable side effects such as internal bleeding when taken in large doses or for long periods. The steroid drugs are also used but have a variety of side effects and can only be used under close medical supervision. Other drugs which have been proposed such as phenylbutazone, indomethacin and chloroquines are only partially effective and also have very serious side effects.

Surprisingly, it has been found that xenylsalate has a pronounced anti-inflammatory action as well as pain killing action when taken internally for the treatment of arthritis.

Xenylsalate, sometimes known as biphenamine, diethylaminoethyl 2-hydroxy-3-phenyl-benzoate, was first synthesized in the 1930's. Although the free base may be used it is preferred to use the hydrochloride; the hydrochloride was employed in the clinical studies detailed later and is referred to as XCl. It has been shown to have a variety of mild biological properties. These properties were antifungal, antibacterial, anesthetic, and analgesic; xenylsalate also manifested a very low acute toxicity in laboratory rats by oral administration. The only actual use of the compound was as an antiseborrheic agent and this has been discontinued. Except for the determination of acute toxicity, all studies were restricted to topical use of comparatively dilute solutions and ointments, approximately 0.01% and 1% respectively.

Attempts to better evaluate the full pharmacological potential of the compound led to tissue culture studies which showed a non-toxic reversible effect on epitherlial cell growth; this effect was wholly unexpected; what was expected was irreversible or lethal effect upon these cells analogous to the effects of the salicylates and other poisons. The essentially complete inhibition of growth and its rapid reversal when the xenylsalate was removed appeared to be a new and unique property.

It was expected from the literature that a mild asprin-like analgesic effect might be obtained but the responses were far beyond that of aspirin or even morphine in the relief of pain. Further, and this was completely unexpected, xenylsalate was found to be extremely effective in relieving inflammation.

DESCRIPTION OF THE PREFERRED EMBODIMENTS

Although some temporary analgesic effect might be anticipated based on the chemical structural analogy to procaine and salicylic acid and on the reports of topical application of dilute solutions and ointments for topical use, the analgesic action obtained by systemic use was far beyond anything that might have been projected. Further, the fact that the analgesic action seemed to be associated with painful edema or inflammation strongly suggested that the xenylsalate control of the pain syndrome might be only a measure of an unexpected anti-inflammatory effect, the pain being only a symptom of the inflammation or edematous condition. It should be emphasized at this point that the prior art had not indicated any anti-inflammatory effects. It was decided to test this hypothesis in human subjects afflicted with clinical conditions where inflammation is the primary pathological problem. This led to preliminary trials in subjects afflicted with arthritis and allied conditions.

The dosage level tentatively established at 0.300 gram orally gave an analgesic effect for 4 hours; posology for the 40 to 50 kg subject was three 0.300 gm. capsules with each meal, plus 0.600 gm. at bedtime if the pain persists overnight. Later the injectable route (intermuscular) was tried and found to give more striking and rapid reversal of the pain syndrome. The I.M. posology for the 40 to 50 kg. human was 2.5 cc. to 5.0 cc. I.M. of a 4% aq. solution in bacteriolstatic water U.S.P. once or twice daily.

The following general clinical management of the arthritic patient was evolved to select chronically ill, stabilized subjects who had been treated by every available therapy, and then permitting subjects to continue with current regimen and life style until they feel they can alter or drop their current therapeutic regimen in favor of xenylsalate therapy.

Repeated administration showed only three minor side effects:

1. If taken orally without food there was occassional gastric distress.
2. In that rare patient whose gastrointestinal tract is hypersensitive to drugs (or where a malabsorption syndrome is obvious) the parenteral (I.M. route must be employed).
3. Parenteral administration gives faster, and more effective clinical response. The only side effect seems to be a slight, transient hypoglycemic episode when inadvertently injected I.V. instead of I.M.

The following case histories illustrate the safety and efficacy of the present invention:

CASE 1

B.C.A. male, age 80, white, retired engineer and business man.

Diagnosis: Degenerative Joint Disease (Osteoarthritis), Coxae Malum Senilis; Stage — far advanced case.

Histories and findings: Initial onset of arthritis began 19 years ago with pain in left hip following a fall while swimming; within a few months he felt pain in shoulders.

Current picture: Right shoulder, fingers, spine with sciatic nerve root irritation, and pronounced limitation of motion of the hips; unable to fully flex and extend spine; wears shoe lift both outside and inside heel. Patient limps and has a definite shortening of the left leg. Right ankle swells occasionally; no other obvious joint swelling. Sleep disturbed by excruciating pain as he moves in bed.

Blood picture is essentially normal. X-ray examination of the lumbrosacral spine, pelvis, hips reveal extensive hypertrophic changes of the entire lumbar region with extensive calcium deposits around L4 and L5 and sacrum, with pronounced ankylosis at these joints. Left femur, neck and head, and acetabulum show marked deformity with destruction of weight bearing cartilage. Findings indicate a long-standing degenerative process, probably senile coxitis. Changes suggest a neurotrophic arthropathy. Further X-rays indicate a 1st degree spondylolisthesis, L4 and L5.

Previous treatment: Butazolidine - no relief; Gold - no relief; Aspirin - heavy dosages; 15 to 25 5gr. aspirins daily, some control of pain but only temporary.

Treatment: XCl therapy was indicated for this patient at least for the type of effective control of pain exhibited by XCl in less severe osteoarthritics; further, regarding the anti-inflammatory potency of XCl, since right ankle swells occasionally, it is likely that there is probably an on-going inflammatory process which might be important in the progression of this disease state. It was decided to concentrate on a fairly heavy initial oral dosage of XCl and then to taper off to an appropriate oral maintenance dosage. The standard placebo controls were employed to eliminate the possibility of an easy placebo response: there was no reaction whatsoever to regular oral or parenteral placebos. The patient continued on aspirin as needed (15 to 25 aspirin tablets daily) to mask the pain. In addition, patient was placed on an oral therapeutic regimen of 300 mg. XCl t.i.d. (with meals) and 600 mg XCl at bedtime. At the end of 72 hours patient reported that most of the pain and discomfort seemed to have disappeared and that he slept well for the first time in years. On his own, he decreased the use of aspirin until by the 15th day he no longer needed aspirin on a regular basis.

Patient continued on the above XCl therapeutic regimen for three months. By this time he was still free of pain and discomfort (no need of aspirin), was walking with less limping, right ankle no longer swells, and right shoulder and fingers functioning quite well. X-ray examination revealed that this patient's longstanding degenerative process has been stopped and there is some evidence to show reconstruction of the various joints. In other words, apparently the degenerative disease process has been reversed and the patient is slowly healing.

The same XCl therapeutic regimen was continued for the first six-month period. At the end of this period the patient was functioning very, very well for his age. Patient now very alert, definite audiovisual improvement, improvement in skin texture (the common "elephant skin" is gone), very active physically including an active sex life with several young women. Left leg seems to have "lengthened" significantly as patient is walking with only a very slight limp. In fact patient has improved so much that he claims his friends no longer recognize him. Patient placed on a permanent XCl maintenance regimen of 150 mg t.i.d., plus 300 mg at bedtime.

CASE 2

F.T., age 47, female, white, former school teacher.

Diagonsis: Rheumatoid arthritis, very severe.

History and Findings: Rheumatoid arthritis involving all joints of the extremities and spine with marked deformity. Duration of condition 27 years. Severe headaches every day, and great difficulty sleeping and great difficulty getting out of bed in the morning. Patient is confined mostly to wheelchair and bed. To make life bearable, patient has taken one to two dozen aspirins daily for the last seven years.

Previous Treatment: Patient subjected to full gamut of conventional arthritis therapies with only temporary improvement at best.

Treatment: Diagnosis confirmed many time by various specialists; sedimentation rate at start of therapy was 49. Subject was instructed to continue her life style unchanged including taking her 24 aspirin tablets each day. She was then subjected to the regular placebo protocol and showed no response. She was then placed on two 150 mg. capsules of XCl t.i.d. with meals and four 150 mg. oral capsules before bedtime taken with fruit or vegetable juice. By the end of the third day she was able to stop her regular use of aspirin. By the end of the tenth day she had about 50% freer movement of all her joints and about 80% relief of pain; she no longer had headaches and was now sleeping well; further, she was able to get out of bed in the morning with only minor discomfort and was able to remain ambulatory during the day. During the next 20 days she was maintained on half the oral dosage (three 150 mg. capsules t.i.d. plus two 150 mg. capsules at bedtime); she required the use of only two aspirin tablets on two occasions to help her get back to sleep when awakening during the night to go to the bathroom. There was a definite decrease in the various deformities; her sedimentation rate had dropped to 32.

At the end of this first 30 days, a second course of therapy was initiated which involved the continuation of her "maintenance dose" of five 150 mg. capsules oral XCl per day plus a series of intramuscular injections of 5.0 cc. of a 4% solution of XCl twice daily: the injections to be continued until no further significant responses are observed. By the end of the 5th day, pain seemed to be completely absent, and apparently complete freedom of movement of joints has now been achieved. Stopped injections but continued patient's "maintenance dose". A regimen of intensive physical therapy was initiated to strengthen all previously afflicted joints and muscles. Three months later patient seemed to be asymptomatic, free of her deformities and leading a normal physical life; no headaches, sleeps well and no aspirin needed. Patient continued on maintenance dose except for a ten-day period (at the end of the 3rd month) to see whether improvement was more than a transitory effect and/or a mere masking of an on-going disease process: this cessation of therapy resulted in no return of any of the original symptoms. Patient is staying on maintenance dosage as a preventive measure. Her sedimentation is apparently slowly dropping, down to 22 at the end of the 4th month.

Patient no longer feels she has arthritis (end of 6 months of XCl and physical therapy); she is slowly reconstructing her life style and is planning to resume her teaching career which her illness forced her to abandon 7 years ago.

CASE 3

W.M., female, age 50, white, housewife.

Diagnosis: Rheumatoid arthritis of the peripheral joints with classical psoriatic skin lesions and marked psoriasis of all finger-nails. The patient probably should be classified as a case of "psoriatic arthritis".

History and Findings: Patient claims that her condition involving arthritis and psoriasis with psoriatic nail changes developed at least 23 years ago. Patient was unable to make a first or grip anything. Both hands, wrists and fingers, swollen, tense and painful. Deep pitting present on digital pressure over hands, indicating considerable edema. Very severe backache and very painful right hip joint with stiffness.

Previous Treatment: Steroids without improvement; Gold without improvment; Salicylates (heavy doses) without improvement; during recent months 20 to 30 aspirin tablets (5 grains or 300 mg each) taken daily.

The examination and laboratory data strongly indicate the coincidence of two concomitant disease states: advanced rheumatoid arthritis and psoriasis. However, since both disease states are considered inflammatory conditions and since XCl is an antiinflammatory agent, it was felt that both disease states, whether related or not, might respond well to XCl therapy. It was decided to initiate oral plus parenteral XCl simultaneously to insure a fast response. Patient was placed on five 150 mg. capsules daily (one with each meal plus two more at bedtime) and given 1 daily intramuscular injection of 5cc. of 4% XCl. Standard placebo protocol used, but patient showed no placebo response whatsoever. With initiation of XCl therapy, patient responded as follows: Day following first injection: pain in hands less severe; swelling decreased ¼ inch over both hands. Patient says she "felt better all over". Day following second injection: slept for first time without pain. No longer felt she needed salicylates and took none. Day following third injection: marked improvement in further reduction of swelling and increased flexibility of both hands. Wrinkling of skin of hands observed with only slight pitting edema. No need for salicylates and took no more.

Following the next three daily injections, patient noted still further subsidence of swelling of wrists and hands with greater flexibility and very little stiffness. Patient observed that big right toe felt normal after being numb for many months. Patient also reported increased energy, and a significant weight loss which she attributed to elimination of retained water in her edematous condition. The psoriatic lesions showed no changes but perhaps more importantly no aggravation or flare-up.

No further injections were given during this initial phase; however, patient has continued the oral posology indicated above. During the next four months, the severe backache and stiff, painful right hip have gradually improved to the point where both back and hip are pain-free and functioning normally, and her psoriatic fingernails had completely cleared without any further evidence of the disease. However, she still had some stiffness of fingers and hands, but this is a minor problem which can probably be resolved by physical therapy.

CASE 4

L. R., female, age 61, former cook.

Diagnosis: Gouty arthritis of the peripheral joints, severe, duration 8 years.

History and Findings: Eight years ago patient suffered an attach of gout involving the thumb of her right hand. Thumb became very swollen and tense with severe pain. This was followed by recurring attacks which gradually also involved her left big toe, neck and knees. There followed a steady progression of the disease with the present picture of high nodules on fingers and toes with great limitation of motion of involved joints. Patient suffered frequently recurring episodes of exacerbation of condition, followed by a steady downward progression with definite deformities of the above joints. On first visit patient presented a picture of chronically ill person; further, tophi were noted on both ears.

Previous Treatment: Colchicine with no relief; Probenecid with no relief; steroids with no relief.

Treatment: Blood picture was within normal limits except the serum uric acid which was 7.5 mg.-%. Patient was checked for placebo response. With regular oral and parenteral placebos, she showed no placebo responses. Patient placed on oral XCl schedule of 150 mg. capsule with each meal plus 300 mg. before bedtime (750 mg. per day). During the first 72 hours, patient reported a significant reduction of pain and discomfort. This treatment schedule was maintained for one month during which time there was further gradual improvement in all symptoms; however, definite traces of the diseased condition remained and it seemed advisable to treat the patient more intensively. While the patient was maintained on the above dosage schedule, the patient was treated twice daily by the intramuscular injection of 2.5 cc of a 4% solution of XCl hydrochloride. After the fourth day (eight injections) patient was free of all joint symptoms, as well as the gouty nodules on feet and hands with complete freedom from pain and the restoration of complete flexibility of all joints. This patient has now been maintained for many months on the original oral dosage schedule. The tophi on both ears have disappeared and to date she has suffered no return of the disease condition.

Serum uric levels gradually returned to normal. Mentally and physically the patient has shown striking improvement since initiation of XCl therapy.

I claim:

1. The method of treating arthritis and related conditions comprising administering systemically to an arthritic patient an effective amount of xenylsalate.

2. The method of claim 1 wherein the xenylsalate is administered orally.

3. The method of claim 1 wherein the xenylsalate is administered intermuscularly.

4. The method of claim 1 wherein the xenylsalate is employed as the hydrochloride salt.

* * * * *